(12) United States Patent
Scheurwater et al.

(10) Patent No.: US 10,709,085 B2
(45) Date of Patent: Jul. 14, 2020

(54) LETTUCE VARIETY '80020-09I1-007'

(71) Applicant: Bejo Zaden BV, Warmenhuizen (NL)

(72) Inventors: Teunis Scheurwater, Nieuw Lekkerland (NL); Roelof Marinus Veenstra, Wieringerwaard (NL); Albertus Johannes Maria Schrijver, Warmenhuizen (NL)

(73) Assignee: Bejo Zaden BV, Warmenhuizen (NL)

( * ) Notice: Subject to any disclaimer, the term of this patent is extended or adjusted under 35 U.S.C. 154(b) by 0 days.

(21) Appl. No.: 16/158,706

(22) Filed: Oct. 12, 2018

(65) Prior Publication Data

US 2019/0110423 A1    Apr. 18, 2019

Related U.S. Application Data

(60) Provisional application No. 62/572,018, filed on Oct. 13, 2017.

(51) Int. Cl.
*A01H 6/14* (2018.01)
*A01H 5/12* (2018.01)

(52) U.S. Cl.
CPC ............. *A01H 6/1472* (2018.05); *A01H 5/12* (2013.01)

(58) Field of Classification Search
None
See application file for complete search history.

(56) References Cited

U.S. PATENT DOCUMENTS

| | | | |
|---|---|---|---|
| 8,530,725 B2 | 9/2013 | Votava | |
| 8,697,359 B1 | 4/2014 | Zhang | |
| 9,521,825 B2 | 12/2016 | Heintzberger et al. | |
| 9,642,331 B1 | 5/2017 | Peng et al. | |
| 9,642,332 B2 | 5/2017 | Heintzberger et al. | |
| 2016/0007552 A1 | 1/2016 | Scheurwater | |
| 2019/0150387 A1* | 5/2019 | Roca | A01H 6/1472 |

FOREIGN PATENT DOCUMENTS

| | | |
|---|---|---|
| NL | 1040073 C | 9/2014 |
| WO | 2014131857 A1 | 9/2014 |

* cited by examiner

*Primary Examiner* — Eileen B O Hara
(74) *Attorney, Agent, or Firm* — The Webb Law Firm

(57) ABSTRACT

Provided herein is a lettuce variety, '80020-09I1-007', including seeds thereof and methods of generating additional lettuce varieties using variety '80020-09I1-007'. Lettuce variety '80020-09I1-007' is characterized by its size, long leaf stalk, color, and resistance to *Bremia lactucae*.

20 Claims, 7 Drawing Sheets
(7 of 7 Drawing Sheet(s) Filed in Color)

LETTUCE VARIETY '80020-09I1-007'

CROSS-REFERENCE TO RELATED APPLICATIONS

The present application claims priority to U.S. Provisional Patent Application No. 62/572,018, filed Oct. 13, 2017, which is incorporated herein by reference in its entirety.

FIELD OF THE INVENTION

Disclosed herein is a new variety of baby leaf lettuce designated '80020-09I1-007'.

BACKGROUND OF THE INVENTION

Cultivated forms of lettuce are members of the highly polymorphic species *Lactuca saliva*, which is grown for its edible head and leaves. Lettuce is one of many members of the Asteraceae family. Other related plant species are, among many, *Apium graveolens* (celery), *Foeniculum vulgare* (fennel) and *Cichorium intybus* (chicory). As a crop, lettuce is grown commercially wherever environmental conditions permit the production of an economically viable yield.

A dicotyledonous species, *L. sativa* is known for the composite flowers made of individual florets. This composite flower is in fact a cluster of many small flowers, where some flowers have specialized in e.g., the "petals" that are actually ribbon-shaped flowers. Inside this area many small flowers or florets are present, each with an ovary, pappus, anthers and a style with stigmas. The florets have five fused petals to form a corolla tube. The flowers mature from the outside toward the center, with the youngest flowers in the middle.

Lettuce was first cultivated in ancient Egypt where it was used for its leaves and oil containing seeds. From there the crop spread to the Greeks and Romans. By 50 A.D., many types of lettuce were already described, and, as with many food crops, lettuce appeared in several mediaeval books, including herbal books. During the 16th through the 18th century many new varieties were developed in Europe, and cultivars from the 18th century still can be found in gardens.

Lettuce cultivars (cultivated varieties) are available in a wide range of leaf colors, leaf shapes, and textures. In addition, lettuce is rich in vitamins (A, K) and is a good source of folate and iron. In dark green lettuce types, like Romaine, higher concentrations of (3-carotene are present. The varied appearance, as well as the nutritional value of lettuce, contributes to the popularity of lettuce as a salad vegetable. Main lettuce types are: butterhead lettuce (round heads filled with thin, pliable leaves, and small, soft head with an almost oily texture) (*L. sativa* var. *capitata*), crisphead (round heads but thick, crisp leaves), which is divided further in Batavia (with open or closed, loosely filled head) (*L. sativa* var. *capitata*) and Iceberg (with overlapping leaves forming a dense firm and closed head) (*L. sativa* var. *capitata*), romaine or cos lettuce (*L. sativa* var. *longifolia*, having elongated upright leaves forming a loose, loaf-shaped head with dark green outer leaves), and leaf, cutting, or baby leaf lettuce (*L. sativa* var. *crispa*, which does not form a head). Most cultivated lettuce types are diploid; where 2n=2x=18.

Lettuce is an open pollinated crop; seeds can be grown easily since flowering plants self-pollinate because the floral structure (with a stylus growing through an anther cylinder) strongly promotes self-pollination. Lettuce is generally grown as a hardy annual; the crop is easily cultivated but requires relatively low temperatures to avoid premature flowering. Moreover, seeds from *L. sativa* are sensitive to high temperatures and soil salinity, both of which can affect germination.

Lettuce in general is an important and valuable vegetable crop. Therefore, it is desirable to develop new varieties of lettuce having novel and exceptional traits,

SUMMARY OF THE INVENTION

Provided herein is lettuce variety '80020-09I1-007', characterized by its color, size, and resistance to various isolates of *Bremia lactucae*. In one aspect, seed of lettuce variety '80020-09I1-007' is provided. Seed of variety '80020-09I1-007' has been deposited with NCIMB under Accession No. 42823.

Also provided herein are plants grown from seed of variety '80020-09I1-007', and plant parts and seeds produced by plants so grown.

Also provided herein are methods of generating offspring of variety '80020-09I1-007', including the steps of crossing a plant of variety '80020-09I1-007' with a second variety of lettuce plant. In aspects, both plants are variety '80020-09I1-007'. In other aspects, the second variety is selected for a desired trait which can be introduced into offspring, such that said offspring include physiological/morphological traits of variety '80020-09I1-007' and the desired trait(s) of the second variety.

BRIEF DESCRIPTION OF THE DRAWINGS

The patent or application file contains at least one drawing executed in color. Copies of this patent or patent application publication with color drawings will be provided by the Office upon request and payment of the necessary fee.

DESCRIPTION OF THE INVENTION

Figure 1:
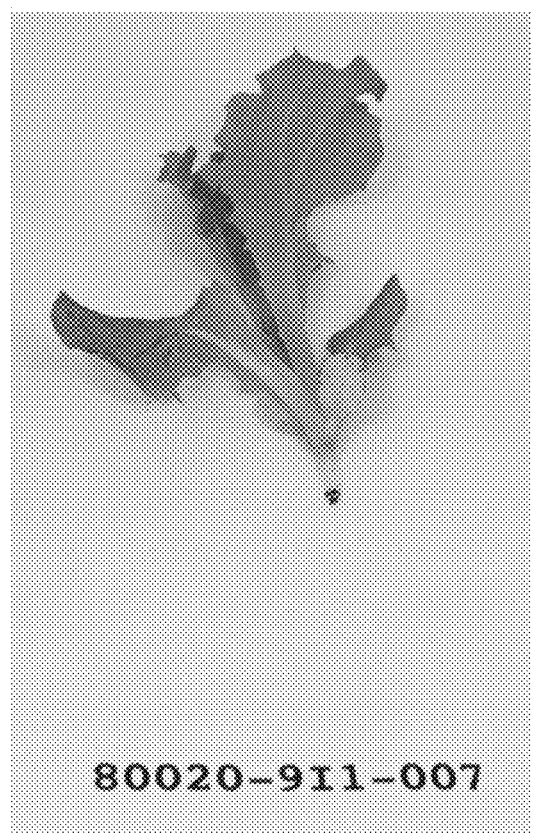
FIG. 1 is an image of lettuce variety '80020-09I1-007'.
Figure 2:
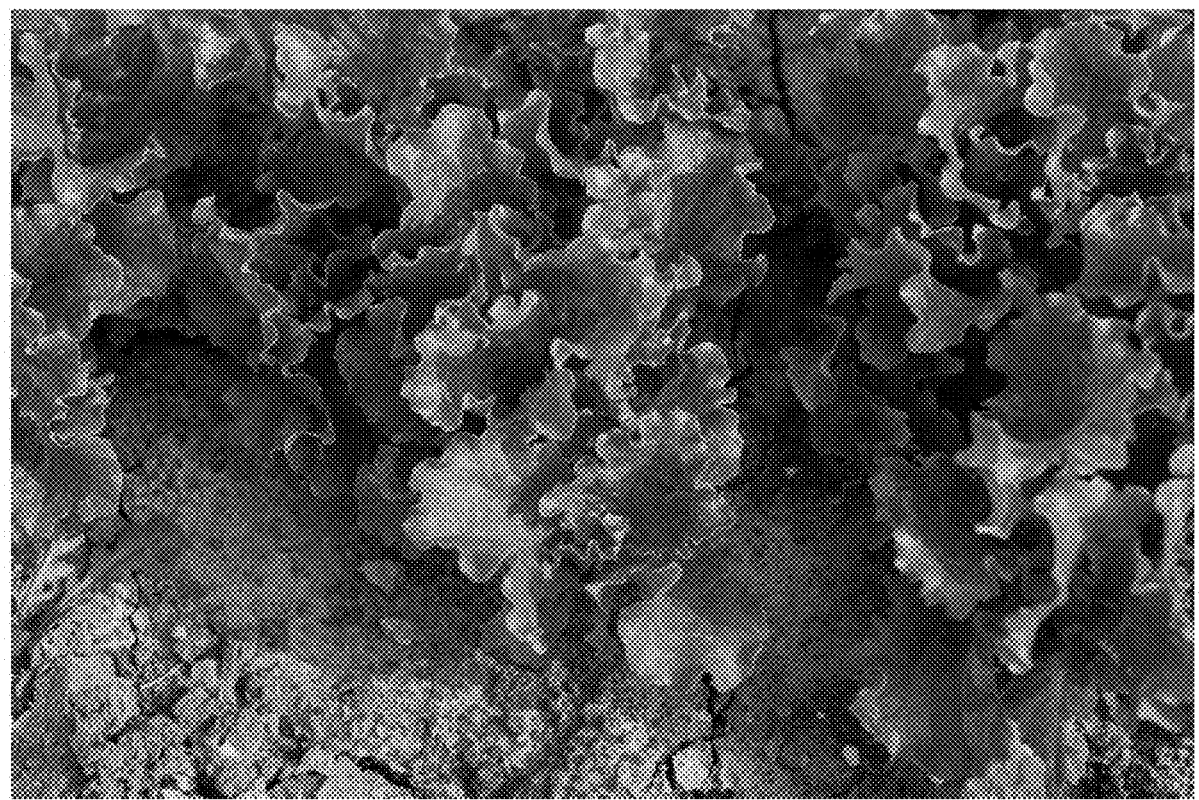
FIG. 2 is an image of lettuce variety '80020-09I1-007'.

In the description and tables which follow, a number of terms are used. In order to provide a clear and consistent understanding of the specification and claims, including the scope to be given such terms, the following definitions are provided:

Amplified Fragment Length Polymorphism (AFLP®). A PCR-based method of identifying polymorphisms through digestion with known restriction enzymes followed by visualization through use of radiography or fluorescence.

Allele. The allele is any of one or more alternative forms of a gene, all of which relate to one trait or characteristic. In a diploid cell or organism, the two alleles of a given gene occupy corresponding loci on a pair of homologous chromosomes.

*Alternaria sonchi*. A fungus of the phylum Ascomycota that causes *Alternaria* leaf spot in *L. sativa*.

Backcrossing. Backcrossing is a process in which a breeder repeatedly crosses hybrid progeny back to one of the parents, for example, a first generation hybrid F1 with one of the parental genotype of the F1 hybrid.

BC1: First backcross generation.

Bolting. The premature development of a flowering stalk, and subsequent seed, before a plant produces a food crop. Bolting is typically caused by late planting when temperatures are low enough to cause vernalization of the plants.

*Bremia lactucae* (Bl). A fungus of the class Oomycete that causes downy mildew in lettuce in cooler growing regions.

Cleaved Amplified Polymorphic Sequence (CAPS). A method of identifying genetic markers based on the length of restriction fragment lengths. Restriction fragments analyzed using CAPS are typically generated using a Restriction Fragment Length Polymorphism assay.

Core diameter. The diameter of the lettuce stem at the base of the cut head.

Core length. Length of the internal lettuce stem measured from the base of the cut and trimmed head to the tip of the stem.

Cotyledon. One of the first leaves of the embryo of a seed plant; typically one or more in monocotyledons, two in dicotyledons, and two or more in gymnosperms.

Clustered Regularly Interspaced Short Palindromic Repeats (CRISPR). Refers to DNA sequences found in bacteria that include portions of DNA introduced to the bacteria by a given virus. The concept is the basis of the CRISPR system of editing an organism's genome (see, e.g., U.S. Pat. No. 8,697,359, incorporated herein by reference in its entirety).

CRISPR-Associated System (CAS). A set of homologous genes, encoding enzymes, that reside in the genome near the site of CRISPR sequences. These enzymes target DNA sequences based on similarity to the viral sequences included in the CRISPR regions.

Embryo. A plant embryo is a portion of the seed including precursors of the leaves, stem, and root, and one or more cotyledons.

*Erwinia carotavora*. Bacteria of the class Gammaproteobacteria that can infect *L. sativa*.

F1, F2, F3 . . . First, second, third, etc. filial generation of offspring of distinctly different parental types.

First water date. The date the seed first receives adequate moisture to germinate. This can and often does equal the planting date.

Frame diameter. The frame diameter is a measurement of the lettuce plant diameter at its widest point, measured from the outer most wrapper leaf tip to the outer most wrapper leaf tip.

Gene. As used herein, "gene" refers to a segment of nucleic acid. A gene can be introduced into a genome of a species, whether from a different species or from the same species, using transformation or various breeding methods.

Genetically-Modified Organism (GMO). An organism whose genome has been altered using some form of genetic engineering.

Green leaf lettuce. A type of lettuce characterized by having curled or incised leaves forming a loose green rosette that does not develop into a compact head.

Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Hypocotyl. The portion of the stem of an embryo plant beneath the cotyledons, but above the root.

Lettuce Big Vein virus (LBV). Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Lettuce Mosaic virus (LMV). A disease that can cause a stunted, deformed, or mottled pattern in young lettuce and yellow, twisted, and deformed leaves in older lettuce.

Marker-assisted recurrent backcrossing (MARB). A method of introducing a single locus of interest. The MARB method allows for maintenance of essential characteristics of the recurrent parent's genome. MARB is particularly effective for Quantitative Trait Loci (QTLs) that are highly variable.

Marker-assisted selection (MAS). A method of selecting a trait of interest based not on the trait, but on a marker associated with that trait.

Market stage. Market stage is the stage when a lettuce plant is ready for commercial lettuce harvest. In the case of an iceberg variety, the head is solid, and has reached an adequate size and weight.

Maturity date. Maturity refers to the stage when the plants are of full size or optimum weight, in marketable form or shape to be of commercial or economic value.

Meristematic cell. Cells of the meristem, which is a collection of undifferentiated cells in the plant. Meristematic cells include apical meristematic cells and lateral meristematic cells.

*Nasonovia ribisnigri*. A lettuce aphid that colonizes the innermost leaves of the lettuce plant, contaminating areas that cannot be treated easily with insecticides.

Pest. A bacterium, fungus, virus, insect, or animal that attacks or negatively affects a plant.

Plant. "Plant" includes plant cells, plant protoplasts, plant cells of tissue culture from which lettuce plants can be regenerated, plant calli, plant clumps and plant cells that are intact in plants, or parts of plants such as pollen, flowers, seeds, leaves, stems and the like.

Promoter. A region of DNA upstream from the start of transcription and involved in recognition and binding of RNA polymerase and other proteins to initiate transcription. A "plant promoter" is a promoter capable of initiating transcription in plant cells.

Protoplast. A plant cell that has had its cell wall at least partially removed.

*Pseudomonas cichorii*. Bacteria of the phylum Proteobacteria that causes leaf blight and spotting in *L. sativa*.

Quantitative Trait Loci (QTL). Refers to genetic loci that control to some degree, numerically representable traits that are usually continuously distributed.

Random Amplified Microsatellite Polymorphism (RAMP). A PCR-based method of identifying polymorphisms through use of simple sequence repeat markers and random amplified DNA polymorphism markers. RAMP is particularly useful for assessing genetic relationships in plant species.

Random Amplified DNA Polymorphism. A PCR-based method of amplifying random sections of DNA.

Ratio of head height/diameter. Head height divided by the head diameter is an indication of the head shape; <1 is flattened, 1=round, and >1 is pointed.

Recurrent Parent. The backcross parent, and member of an identifiable lineage or line that is improved by addition of a trait not found in that line.

Regeneration. Regeneration refers to the development of a plant from tissue culture.

Resistance. The character of a plant to restrict or even inhibit the development of a pest or pathogen in or on the plant and also the restriction of damage these organisms may cause; all in comparison to a susceptible variety and under comparable circumstances.

Restriction Fragment Length Polymorphism (RFLP). A marker in homologous DNA detectable based on fragments of different, specific lengths generated by known restriction enzymes.

Root tip. The terminal portion of the root of a plant.

Royal Horticultural Society of England (RHS). An organization that publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Romaine lettuce. A lettuce variety having elongated upright leaves forming a loose, loaf-shaped head and the outer leaves are usually dark green.

Simple sequence repeats (SSR). A DNA sequence having a number of motifs that are repeated.

Single nucleotide polymorphism (SNP). A common nucleotide variation at a given locus among a given population.

Tomato spotted wilt virus (TSWV). An RNA-containing virus of the genus Tospovirus that can infect *L. sativa* as well.

Transgenic. An organism that contains genetic material from an unrelated organism that has been artificially introduced thereto.

*Xanthomonas campestris*. Bacteria of the phylum Proteobacteria that causes black rot in *L. sativa*.

Lettuce variety '80020-09I1-007'

Provided herein is lettuce variety '80020-09I1-007,' a dark green Batavia lettuce variety suitable for babyleaf production in the spring, summer, and autumn harvesting seasons in the coastal areas of California, and in the late autumn, winter, and early spring harvesting seasons in the southwest deserts of California and Arizona. Lettuce variety '80020-09I1-007' is the result of a cross and a backcross of a Batavia babyleaf variety and a breeding line obtained from a wild lettuce and an older Batavia variety. From the self-pollinated BC1-plant subsequently numerous generations were of individual plant selected. These plants were chosen for their very dark color, disease resistance for *Bremia lactucae*, thick leaves, and long leaf-stalk.

Lettuce variety '80020-09I1-007' has shown uniformity and stability for these traits, within the limits of environmental influence for the traits. It has been self-pollinated through a sufficient number of generations with careful attention to uniformity of plant type. The variety has been propagated with continuous attention for uniformity.

Breeding History

Crosses were made by spraying or misting water over the flowers, thus inactivating pollen present on these flowers. This treatment enables the cross pollination of *Lactuca* plants.

F1 plants can be self-pollinated to produce the F2 generation etc.

Batavia babyleaf breeding line BL0009 was used as a female line to manually cross breeding lines 80006-02K1-002, 80006-02K1-004, 80006-02K1-010, 80006-02K1-012, 80006-02K1-013, 80006-02K1-037, and 80006-02K1-038 as males.

The male lines are disclosed in Netherlands Patent No. NL1040073 and International Patent Publication No. WO 2014/131857, each of which is incorporated by reference herein in its entirety.

From these crosses, 42 F1-plants were identified and all 42 plants were allowed to self-fertilize individually; seeds were collected individually from each F1 plant yielding the F2 generation.

A population of 735 F2 plants was then established. The plants were raised in a nursery. From this population, 44 individual F2 plants were selected and seeds were harvested individually from each plant after self-pollination, yielding the F3 generation.

After testing all individual F3-plants for resistance to *Bremia lactucae*, a total of 36 F3 families were sown. From 14 out of the initial 36 F3 families, 140 individual plants were selected; seeds were harvested after individual self-pollination of these plants, yielding the F4 generation.

All individual F4-plants were tested for *Bremia* resistance. A total of 108 F4-lines were established and 89 individual plants were selected from 11 out of these initial 108 F4 lines. Seeds were harvested after individual self-pollination of these plants, yielding the F5 generation.

All individual F5-plants were tested for *Bremia* resistance. A total of 81 F5-lines were established and 110 individual plants were selected from 17 out of these F5-lines. Seeds were harvested after individual self-pollination of these plants, yielding the F6 generation.

All individual F6-plants were tested for *Bremia* resistance. A total of 99 F6-lines were established and F6-line 80020-06F1-090 showed highly uniform and very desirable horticultural characteristics.

Seeds of all plants from F6 line 80020-06F1-090 were collectively harvested and designated lettuce babyleaf variety '80020-09I1-007'. A deposit of seeds of '80020-09I1-007' disclosed above and recited in the appended claims has been made with the National Collections of Industrial. Food and Marine Bacteria (NCIMB), Ferguson Building, Craibstone Estate, Bucksburn, Aberdeen AB21 9YA, United Kingdom. The date of the deposit was Sep. 27, 2017. All restrictions will be irrevocably removed upon granting of a patent, and the deposit is intended to meet all of the requirements of 37 C.F.R. §§ 1.801-1.809. The NCIMB Accession Number is 42823. The deposit will be maintained in the depository for a period of thirty years, or five years after the last request, or for the enforceable life of the patent, whichever is longer, and will be replaced as necessary during that period.

Variety Description

Figure 3:
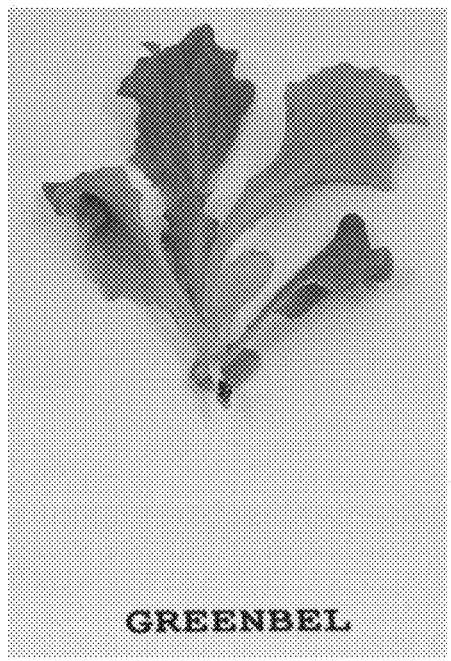
FIG. 3 is an image of a prior lettuce variety 'Greenbel'.
Figure 4:
FIG. 4 is an image of a prior lettuce variety 'Greenbel'.
Figure 5:
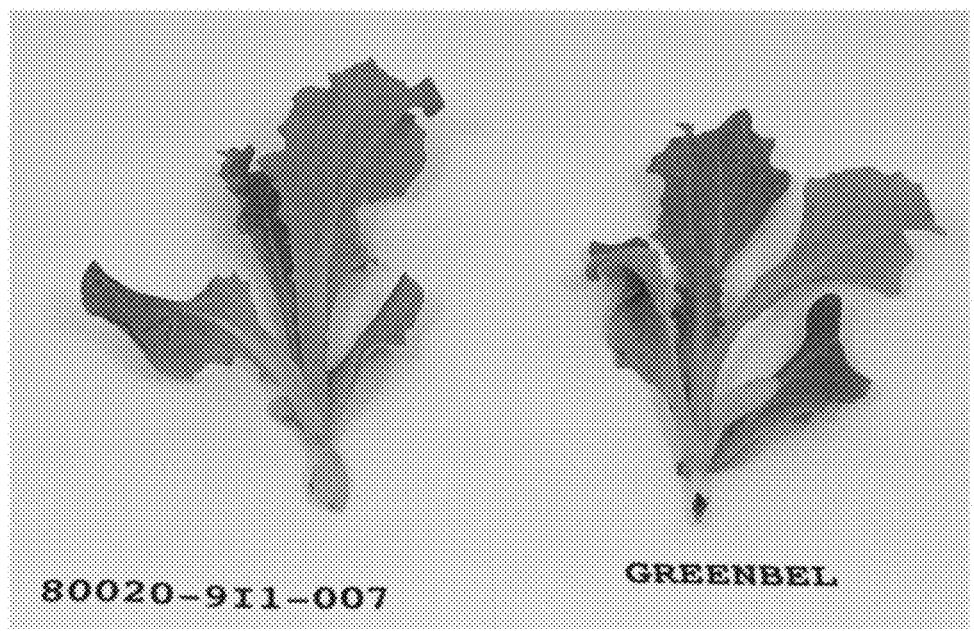
FIG. 5 is an image showing both lettuce variety '80020-09I1-007' and prior lettuce variety 'Greenbel'.
Figure 6:
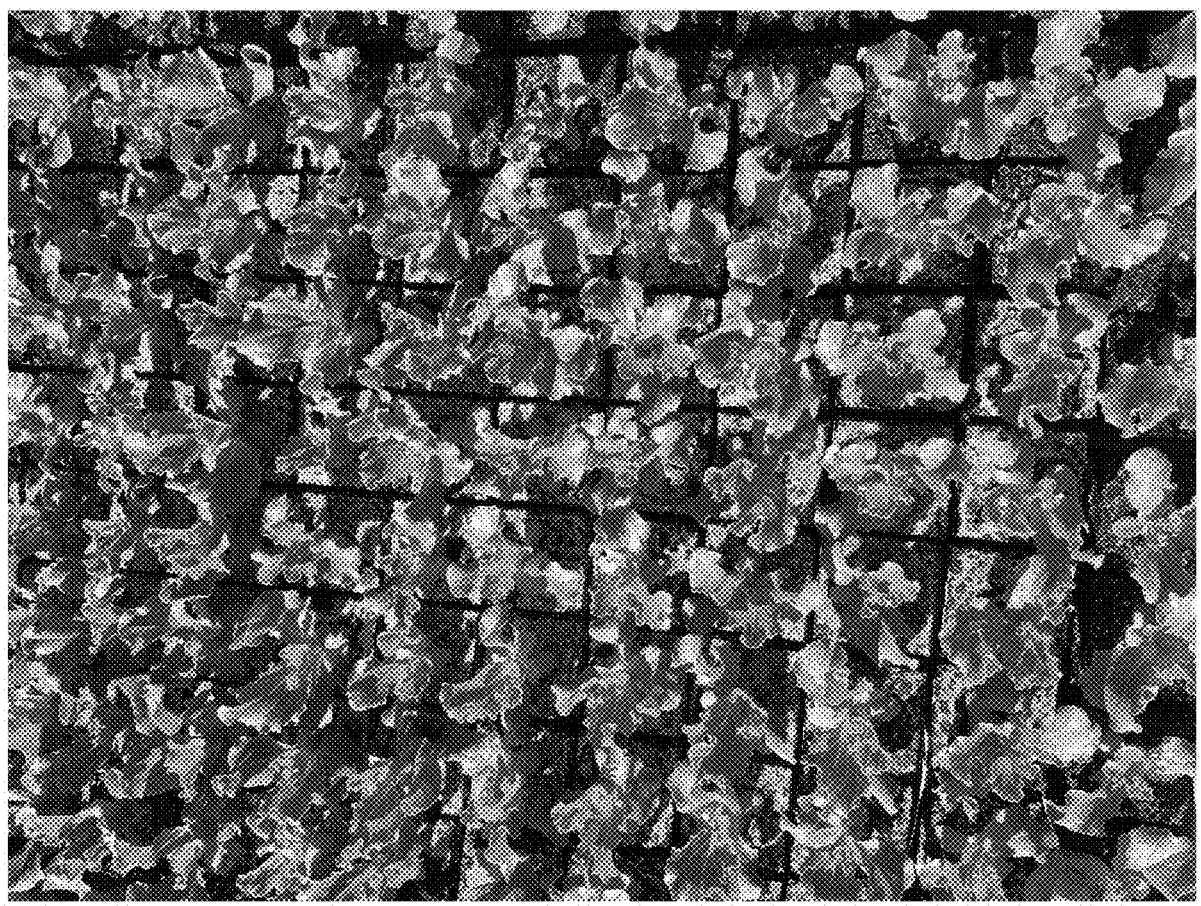
FIG. 6 is an image of lettuce variety '80020-09I1-007'.
Figure 7:
FIG. 7 is an image of lettuce variety '80020-09I1-007'.

Lettuce variety '80020-09I1-007' is a babyleaf lettuce which is open pollinated. FIGS. 1, 2, 6, and 7 show variety '80020-09I1-007' in close up (FIGS. 1 and 7), in the field (FIG. 2), and in plugs (FIG. 6). FIGS. 3 and 4 show a comparison variety, 'Greenbel'. FIG. 5 shows variety '80020-09I1-007' and 'Greenbel' in a close up, for comparison. Variety '80020-09I1-007 is resistant to at least *Bremia lactucae* isolates Bl: 16-33 and to *Nasonovia ribisnigri*:0 and, with regard to 'Greenbel', exhibits greater weight, shorter leaf length, and increased leaf width and darker green color at the upper leaves.

Characteristics of 80020-09I1-007' in concordance with the applicable UPOV Questionnaire are provided below in Tables 1-3.

TABLE 1

| | |
|---|---|
| Seed color | Black |
| Dormancy | Yes, after production |
| Leaf: | |
| Hue of outer leaves | Greyish |
| Anthocyanin Coloration | Absent |
| Intensity of coloration of outer leaves | Very dark |
| Bolting time (long day conditions) | Very early |
| Resistance to *Bremia lactucae* isolate B1: 16 | Present |
| Growth type at maturity | Cutting or gathering lettuce type |
| Culture type | Open |
| Growing season | Spring/Summer/Autumn |

TABLE 2

| | |
|---|---|
| Plant: | *Lactuca sativa* '80020-09I1-007' |
| Type: | Cutting or gathering lettuce; or babyleaf lettuce |
| Seed: | |
| Color: | black |
| Light dormancy: | — |
| Heat dormancy: | — |
| Mature leaves | |
| Margin: | Tortured |
| Green color (at harvest maturity): | Greyish ** |
| Intensity of color of outer leaves | very dark ** |
| Anthocyan distribution | absent |
| Leaf attitude at 10-12$^{th}$ leaf stage | Semi-erect |
| Leaf blade (at 10$^{th}$-12$^{th}$ leaf stage) | entire |
| Glossiness | Medium to strong |
| Thickness | Thick to very thick |
| Plant (at market stage) | |
| Height: | 6-8 cm |
| Head size class | No head, gathering type |
| Shape | Gathering type |
| Bolting | Very early |
| Number of days from first water date to first flower | (very early) |
| Height of mature seed stalk | 50-60 cm |
| Spring area | coastal areas of California SW deserts of California and Arizona |
| Summer area | coastal areas of California |
| Autumn area | coastal areas of California southwestern deserts of California and Arizona |
| Winter area | southwestern deserts of California and Arizona |
| Disease/pest resistance | |
| Lettuce Necrotic Stunt Virus LNSV | absent |
| Lettuce Mosaic Virus | absent |
| Lettuce Big Vein Virus LBVV | absent |
| Downey Mildew | B1: 16-33 |
| Lettuce aphid | Resistant (Nr: 0) |
| Cold weather bolting | Very early |

TABLE 3

Characteristics of Variety '80020-09I1-007' Based on Naktuinbouw Calibration Book, *L. sativa*, Ver. 1 (2010).

| group | Character | State of expression |
|---|---|---|
| 0 | Plant type | Cutting/gathering lettuce (5) |
| 1 | Seed color | Black (3) |
| 2 | Seedling, anthocyanin coloration | Absent (1) |
| 3 | Leaf attitude at 10$^{th}$-12$^{th}$ leaf stage | Semi-erect (3) |
| 4 | Leaf blade division at 10$^{th}$-12$^{th}$ leaf stage | Entire (1) |
| 5 | Plant diameter | Very small (1) or n.a.: no head formation |
| 6 | Plant head formation | No head (1) |
| 7 | Leaf: thickness | Thick to very thick (8) |
| 8 | Leaf: attitude at harvest maturity | Semi-erect (3) |
| 9 | Leaf shape | Medium elliptic (2) |
| 10 | Leaf: shape of tip | Rounded (3) |
| 11 | Leaf: hue of green color outer leaves | Greyish (3). |
| 12 | Leaf: intensity of color outer leaves | Very dark (9) |
| 13 | Leaf: anthocyanin coloration | Absent (1) |
| 14 | Leaf: intensity of anthocyanin coloration | Very weak (1) |
| 15 | Leaf: glossiness of upper side | Medium to strong (6) |
| 16 | Leaf: blistering | Absent/very weak (1) |
| 17 | Leaf: size of blisters | Very small (1) |
| 18 | Leaf: degree of undulation of margins | Medium to strong (6) |
| 19 | Leaf blade: incisions of margins apical part | Absent (1) |
| 20 | Leaf blade: depth of incisions apical part | Very shallow (1) |
| 21 | Leaf blade: density of incisions ap. part | Very sparse (1) |
| 22 | Leaf blade: type of incisions on apical part | Sinuate (1) |
| 23 | Leaf blade venation | Not flabellate (1) |
| 24 | Axillary sprouting | Absent or very weak (1) |
| 25 | Time to harvest maturity | Very early (1) |
| 26 | Time to beginning of bolting (long day) | Very early (1) |
| 27 | Plant height (flowering) | Short (3) |
| 28 | Plant fasciation | Absent (1) |
| 29 | Plant intensity of fasciation | Very weak (1) |
| 30 | Resistance to downy mildew | B1: 16-33 |

Additional characteristics of 80020-09I1-007', in comparison with variety 'Greenbel', are provided below in Tables 4-7.

TABLE 4

Weight

| Variety | '80020-09I1-007' | 'Greenbel' |
|---|---|---|
| Count | 50 | 50 |
| Sum | 78.94 | 64.25 |
| Mean | 1.579 | 1.285 |
| Maximum value | 2.06 | 2.14 |
| Minimum value | 0.84 | 0.89 |
| Variance | 0.098 | 0.081 |
| Std. deviation | 0.314 | 0.285 |
| Joint variance | 0.1107 | |
| Degrees of freedom | 98 | |
| t-statistic | 4.90 | |
| P-value | 3.75E−06 | |
| Confidence level % | 100.000 | |

TABLE 5

Leaf Length (mm)

| Variety | '80020-09I1-007' | 'Greenbel' |
|---|---|---|
| Count | 50 | 50 |
| Sum | 3124 | 3400 |
| Mean | 62.480 | 68.000 |
| Maximum value | 83 | 94 |
| Minimum value | 42 | 57 |
| Variance | 39.193 | 72.898 |
| Std. deviation | 6.260 | 8.538 |

TABLE 5-continued

Leaf Length (mm)

| Variety | '80020-09I1-007' | 'Greenbel' |
|---|---|---|
| Joint variance | | 63.1741 |
| Degrees of freedom | | 89.87 |
| t-statistic | | 3.69 |
| P-value | | 3.88E−04 |
| Confidence level % | | 99.96 |

TABLE 6

Leaf Width (mm)

| Variety | '80020-09I1-007' | 'Greenbel' |
|---|---|---|
| Count | 50 | 50 |
| Sum | 1537 | 1429 |
| Mean | 30.740 | 28.580 |
| Maximum value | 38 | 37 |
| Minimum value | 20 | 22 |
| Variance | 12.482 | 9.677 |
| Std. deviation | 3.533 | 3.111 |
| Joint variance | | 12.1459 |
| Degrees of freedom | | 98 |
| t-statistic | | 3.24 |
| P-value | | 1.61E−03 |
| Confidence level % | | 99.84 |

TABLE 7

RHS Color

| Variety | '80020-09I1-007' | 'Greenbel' |
|---|---|---|
| Upper side leaf | 137B | 146A |
| Lower side leaf | 146B | 146B |

Sowing date: Aug. 16, 2017
Assessment date: Sep. 27, 2017.
1 gram seeds/m$^2$
Climatic conditions: most of the time sunny or moderately clouded; some rainfall.
Temperature: Daytime 15-20° C.
  Nighttime 10-14° C.

Further Embodiments

In general, breeding goals associated with development of any plant, including lettuce, include: head architecture, weight, size leaf color, shape, texture, flavor, earliness, slow bolting, short core, good germination, high yield, uniformity at maturity, improved shelf life, resistances against pests and physical disorders, and hybrid production.

Lettuce breeding now is accelerated by application of several techniques including tissue culture for enabling wide crosses and protoplast fusions. Further great progress is made, as with breeding of many vegetable crops, by applying molecular markers. Developing these markers has led to the development of increasingly detailed genetic maps. Genomic data and maps are available for example from the University of California at Davis Lettuce Genome Resource.

These maps contain data from several sources and multiple populations and comprise Quantitative Trait Loci (QTLs), and markers linked to monogenic traits. These markers can be e.g., RFLP, AFLP, CAPS, RAMP, SSR, microsatellites, and/or SNP markers which all are well known for persons skilled in the art; and also sequencing of (parts of the) *Lactuca* genome is established. Application of these techniques also enables MAS/MARB.

As noted above, one goal of breeding in *L. sativa* is resistance to pests. As with many crops, lettuce can be plagued with several physiological problems like nutrient deficiencies but also by pests (nematodes, insects, mammals, bacteria, fungi, and/or viruses) and disease caused thereby. Specific examples include bacterial diseases caused by *Xanthomonas campestris*, *Erwinia carotavora*, and *Pseudomonas cichorii*, fungal diseases caused by *Alternaria sonchi*, *Bremia lactucae*, and *Sclerotinia sclerotiorum*, and viral diseases caused by Lettuce mosaic virus (LMV), Tomato spotted wilt virus (TSWV), and Lettuce big vein virus (LBVV). Insects, in particular *Nasonovia ribisnigri* (lettuce aphid), can be an important vector for spreading viral diseases.

It is a major goal for breeders to develop plant material which has resistance to many of these diseases. This has led to, among others, material, which is resistant to various strains of *Bremia lactucae*, such as described in Patent Application WO 2014/131857, incorporated herein by reference in its entirety.

As noted above, knowledge of *L. sativa* genetics has allowed for extensive mapping of the genome, including 50 genes related to resistance to seven major diseases. Modern molecular techniques also create the possibility to stack genes, including for genes for *Bremia* resistance.

It is feasible to introduce traits by cis-genes from *L. sativa*, or transgenes from any source, encoding novel forms of disease resistance, herbicide resistance, and resistance to pests by, among other techniques, siRNA (host induced gene silencing) as well as other methods which are common to the person skilled in the art.

These methods include, for example and without limitation, electroporation, *Agrobacterium*-mediated transformation, particle gun transformation, polyethylene glycol (PEG)-mediated protoplast transformation, and silicon whiskers transformation. Further, novel molecular techniques as CRISPR/CAS9 can be applied for genome editing purposes. Such techniques are known to those of skill in the art.

Introducing resistance to a pest or disease, either by conventional breeding or applying techniques as described above, provides an alternative to application of chemical protectants; which is expensive and also has a negative impact on the environment, on growers, and other workers with the crop.

Further Embodiments—Genetic Engineering

With the advent of molecular biological techniques, such as those described above and incorporated by reference, that have allowed the isolation and characterization of genes that encode specific protein products, scientists in the field of plant biology have developed a strong interest in engineering the genome of plants to contain and express foreign genes, or additional, or modified versions of native, or endogenous, genes (driven by different promoters) in order to alter the traits of a plant in a specific manner. Any DNA sequences, whether from a different species (i.e. transgenes) or from the same species (i.e. cis-genes), which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of variety '80020-09I1-

007'. Suitable genetic engineering techniques for transforming, or introducing, traits into lettuce variety '80020-09I1-007' include, for example and without limitation, microinjection, biolistics, electroporation, chemical poration, and transformation using vectors.

Accordingly, provided herein are methods of transforming a plant or plant part of lettuce variety '80020-09I1-007,' or offspring thereof, by any transformation method known to those of skill in the art. A particularly common example of plant transformation involves the construction of an expression vector that will function in plant cells. Such a vector comprises DNA comprising a gene under control of, or operatively linked to, a regulatory element (for example, a promoter). The expression vector may contain one or more operably linked gene/regulatory element combinations. The vector(s) may be in the form of a plasmid, and can be used alone or in combination with other plasmids, to provide transformed lettuce plants using transformation methods as described in U.S. Pat. No. 8,530,725, which is incorporated herein by reference in its entirety, to incorporate transgenes into the genetic material of the lettuce plant(s).

Lettuce variety '80020 09I1-007' and offspring thereof can be genetically engineered to express various phenotypes of agronomic interest. Exemplary genes implicated in this regard are those that confer resistance to pests and/or herbicides, genes that confer or contribute to a value-added trait, and genes that control male sterility. Examples of desirable traits for lettuce are known to those of skill in the art and are disclosed in U.S. Pat. No. 8,530,725, which is incorporated herein by reference in its entirety. Methods for transforming lettuce plants or introducing desired traits are similarly disclosed in U.S. Pat. Nos. 8,530,725 and 9,642,331, which are incorporated herein by reference in their entirety.

Further Embodiments—Additional Breeding Methods

Also provided herein are methods for producing a lettuce plant by crossing a first parent lettuce plant with a second parent lettuce plant wherein the first or second parent lettuce plant is a lettuce plant of variety '80020 09I1-007'. Those of skill in the art understand plant breeding techniques, including crossing, thus crossing variety '80020 09I1-007' with another plant of variety '80020 09I1-007', or with another variety (related or unrelated to variety '80020 09I1-007') is well within the skill of the ordinary artisan. Thus, any such methods using lettuce variety '80020 09I1-007' should be considered part of this invention: selfing, backcrosses, hybrid production, crosses to populations, and the like. All plants produced using lettuce variety '80020 09I1-007' as at least one parent are within the scope of the disclosure, including those developed from varieties derived from lettuce variety '80020 09I1-007'.

In aspects of a breeding method described herein, both first and second parent lettuce plants are of lettuce variety '80020 09I1-007'.

In other aspects, lettuce variety '80020 09I1-007' can be used in crosses with other, different, lettuce plants to produce the first generation (F1) lettuce hybrid seeds and plants with superior characteristics. Lettuce variety '80020 09I1-007' can also be used for transformation where exogenous genes are introduced and expressed. Genetic variants created either through traditional breeding methods using lettuce variety '80020 09I1-007' or through transformation of variety '80020 09I1-007' by any of a number of protocols known to those of skill in the art are intended to be within the scope of the present invention.

In one aspect, the method includes the steps of: obtaining the lettuce plant, or a part thereof, of variety '80020 09I1-007', utilizing said plant or plant part as a source of breeding material, and selecting a lettuce variety '80020 09I1-007' progeny plant with molecular markers in common with variety '80020 09I1-007' and/or with morphological and/or physiological characteristics selected from the characteristics of variety '80020-09I1-007' listed in Tables 1-7. Breeding steps that may be used include pedigree breeding, backcrossing, mutation breeding, and recurrent selection. As noted above, such breeding methods are known to those of skill in the art and are disclosed in, for example, U.S. Pat. Nos. 8,530,725 and 9,642,331, which are incorporated herein by reference in their entirety. In conjunction with these steps, techniques such as RFLP-enhanced selection, genetic marker enhanced selection (for example, SSR markers), and the making of double haploids may be utilized.

In another aspect the method includes producing a population of lettuce variety '80020 09I1-007' progeny lettuce plants, comprising crossing variety '80020 09I1-007' with another lettuce plant, thereby producing a population of lettuce plants, which, on average, derive 50% of their alleles from lettuce variety '80020 09I1-007'. A plant of this population may be selected and repeatedly selfed or sibbed with a lettuce plant resulting from these successive filial generations, or may be backcrossed with a recurrent parent ('80020 09I1-007'). One aspect of this invention is the lettuce produced by this method and that has obtained at least 50%, at least 60%, at least 70%, at least 80%, at least 90% or more, all subranges and percentages therebetween inclusive, of its alleles from lettuce variety '80020-09I1-007'. Methods for determining genetic makeup of (genotyping) a lettuce plant are disclosed in, for example and without limitation, U.S. Pat. No. 9,642,332, which is incorporated by reference herein in its entirety.

One of ordinary skill in the art of plant breeding would know how to evaluate the traits of two plant varieties to determine if there is no significant difference between the two traits expressed by those varieties. Thus, the present invention includes lettuce variety '80020 09I1-007' progeny lettuce plants comprising a combination of at least two traits of variety '80020 09I1-007' selected from those listed in Tables 1-7, so that said progeny lettuce plant is not significantly different for said traits than lettuce variety '80020 09I1-007' as determined at the 5% significance level when grown in the same environmental conditions. Using techniques described herein, molecular markers may be used to identify said progeny plant as a lettuce variety '80020 09I1-007' progeny plant. Mean trait values may be used to determine whether trait differences are significant, and preferably the traits are measured on plants grown under the same environmental conditions.

The invention claimed is:

1. A seed of lettuce variety '80020-09I1-007', wherein a representative sample of seed of said variety was deposited under NCIMB Accession No. 42823.

2. A lettuce plant, part thereof, or tissue culture produced by growing the seed of claim 1.

3. A tissue culture produced from protoplasts or cells from the plant of claim 2, wherein said cells or protoplasts are produced from a plant part selected from the group consisting of leaf, pollen, embryo, cotyledon, hypocotyl, meristematic cell root, root tip, pistil, anther, ovule, flower, shoot, stem, seed, and petiole.

4. A lettuce plant regenerated from the tissue culture of claim 3, wherein the plant has all of the morphological and physiological characteristics of variety '80020-09I1-007'.

5. A method for producing a lettuce seed comprising crossing two lettuce plants and harvesting the resultant lettuce seed, wherein at least one of the two lettuce plants is the lettuce plant of claim 2.

6. The method of claim 5, wherein one of the two lettuce plants is a lettuce plant that is unrelated to variety '80020-09I1-007'.

7. An F1 lettuce seed produced by the method of claim 5.

8. A lettuce plant, part thereof, or tissue culture produced by growing the seed of claim 7.

9. A method of introducing one or more desired traits into lettuce variety '80020-09I1-007' comprising:
  (a) crossing a lettuce plant of variety '80020-09I1-007', wherein a representative sample of seed was deposited under NCIMB Accession No. 42823, with a plant of another lettuce variety that comprises one or more desired traits to produce progeny plants, wherein the one or more desired traits is selected from the group consisting of male sterility, herbicide resistance, pest resistance, modified bolting, and resistance to bacterial disease, fungal disease, or viral disease;
  (b) selecting one or more progeny plants that have the one or more desired traits to produce selected progeny plants;
  (c) crossing the selected progeny plants with the lettuce plant of variety '80020-09I1-007' to produce backcross progeny plants;
  (d) selecting for backcross progeny plants that have the one or more desired traits and all of the physiological and morphological characteristics of lettuce variety '80020-09I1-007'; and
  (e) repeating steps (c) and (d) two or more times in succession to produce selected third or higher backcross progeny plants that comprise the one or more desired traits and all of the physiological and morphological characteristics of lettuce variety '80020-09I1-007'.

10. A lettuce plant produced by the method of claim 9, wherein said lettuce plant has the one or more desired traits.

11. The lettuce plant of claim 10, wherein the one or more desired traits is one or more of herbicide resistance, pest resistance, and male sterility.

12. The lettuce plant of claim 10, wherein the desired trait is resistance to a pest other than *Bremia lactucae*.

13. A seed, plant part, or tissue culture of the plant of claim 10.

14. A method of introducing one or more desired traits into lettuce variety '80020-09I1-007' comprising introducing a gene conferring a desired trait into the plant of claim 2.

15. A lettuce plant produced by the method of claim 14, wherein said lettuce plant has one or more desired traits.

16. The lettuce plant of claim 15, wherein the one or more desired trait is one or more of herbicide resistance, pest resistance, and male sterility.

17. The lettuce plant of claim 15, wherein the desired trait is resistance to a pest other than *Bremia lactucae*.

18. A seed, plant part, or tissue culture of the plant of claim 15.

19. A lettuce plant designated '80020-09I1-007', representative seed of which having been deposited under NCIMB Accession No. 42823, wherein said plant comprises at least resistance to *Bremia lactucae* isolates Bl: 16-33 and resistance to *Nasonovia ribisnigri* biotype 0.

20. A seed, plant part, or tissue culture of the plant of claim 19.

* * * * *

UNITED STATES PATENT AND TRADEMARK OFFICE
CERTIFICATE OF CORRECTION

PATENT NO. : 10,709,085 B2
APPLICATION NO. : 16/158706
DATED : July 14, 2020
INVENTOR(S) : Teunis Scheurwater et al.

It is certified that error appears in the above-identified patent and that said Letters Patent is hereby corrected as shown below:

On the Title Page

Item (54), and in the Specification Column 1, Line 1, delete "`80020-0911-007`" and insert -- `80020-09I1-007` --

Signed and Sealed this
Twelfth Day of January, 2021

Andrei Iancu
*Director of the United States Patent and Trademark Office*